United States Patent [19]
Cutler

[11] Patent Number: 6,114,387
[45] Date of Patent: Sep. 5, 2000

US006114387A

[54] PHARMACEUTICAL COMPOSITION FOR ORAL ADMINISTRATION OF CHELATING AGENTS

[76] Inventor: Paul Cutler, 652 Elmwood Ave., Niagara Fa, N.Y. 14301

[21] Appl. No.: 09/505,403

[22] Filed: Feb. 16, 2000

[51] Int. Cl.[7] .................................................. A61K 31/195
[52] U.S. Cl. ........................................... 514/562; 514/566
[58] Field of Search ...................................... 514/562, 566

[56] References Cited

U.S. PATENT DOCUMENTS

| | | | |
|---|---|---|---|
| 5,080,906 | 1/1992 | Carenzi et al. | 424/452 |
| 5,114,974 | 5/1992 | Rubin | 514/566 |

OTHER PUBLICATIONS

Schroeder, "A Practical Method For the Reduction of Plasma Cholesterol in Man", *Journal of Chronic Diseases*, 1956, vol. 4. No. 5, pp. 461–468.

Banner, W., et al, "Experimental Chelation Therapy in Chromium, Lead, and Boron Intoxication With N–Acetyl-cysteine and Other Compounds", *Toxicology and Applied Pharmacology*, 1986, vol. 83, pp. 142–147.

Peters, Henry, et al., "Turkish Epidemic Hexachlorobenzene Porphyria: A 30–Year Study", *Annals of the New York Academy of Sciences*, (Mechanisms of Chemical—Induced Porphyrinopathies), 1987, vol. 514, pp. 183–189.

Brumas, V., et al., "Can N–Acetyl–L–cysteine Affect Zinc Metabolism When Used as a Paractamol Antidote", *Agents Actions*, 1992, vol. 36, pp. 278–188.

Kelation PlusWeb Page, Jan. 27, 2000.

Vibrant Life Web Page, Jan. 19, 2000.

*Primary Examiner*—Raymond Henley, III
*Attorney, Agent, or Firm*—Jaeckle Fleischmann & Mugel, LLP

[57] ABSTRACT

A solid pharmaceutical composition for the oral administration of chelating agents to an individual consists essentially of: at least 100 milligrams of ethylenediaminetetraacetic acid (EDTA) or a molar equivalent amount of pharmaceutically acceptable salts or hydrated salts of EDTA, at least 75 milligrams of N-acetyl-L-cysteine, and an appropriate amount of at least one pharmaceutical formulating agent.

9 Claims, No Drawings

PHARMACEUTICAL COMPOSITION FOR ORAL ADMINISTRATION OF CHELATING AGENTS

FIELD OF THE INVENTION

The present invention relates to chelators for metals and, more particularly, to a pharmaceutical composition for oral administration of chelators to a subject.

BACKGROUND OF THE INVENTION

Chelating agents, or chelators, constitute a well known type of multifunctional organic compounds that are capable of forming complexes of multivalent metal ions such as, for example, calcium, magnesium, zinc, iron, chromium, and lead. Chelators find use in a variety of commercial applications, for example, photographic processing solutions, to which they can be added to form soluble complexes with metal ions that would otherwise produce undesirable precipitates or sludges.

A well known and widely used chelator is ethylenediaminetetraacetic acid, $(HO_2CCH_2)_2NCH_2CH_2N(CH_2CO_2H)_2$, commonly referred to as EDTA, commercially available both as the free acid and as various salts, for example, disodium EDTA, tetrasodium EDTA, dipotassium EDTA, calcium disodium EDTA, etc. Other commercial chelators are the naturally occurring amino acid L-cysteine, $HSCH_2CH(NH_2)CO_2H$, and its acetylated derivative N-acetyl-L-cysteine, $HSCH_2CH(NHCOCH_3)CO_2H$, commonly referred to as NAC.

In addition to their industrial applications, chelators have also been extensively employed therapeutically in the treatment of human subjects. For example, injections of EDTA have been used to remove high levels of toxic lead from the bloodstream of individuals who have been exposed to lead paint. Intravenous injection of chelators has also been employed in the treatment of other medical conditions. For example, U.S. Pat. No. 5,114,974 to Rubin discloses the treatment of atherosclereosis with $MgNa_2EDTA$.

Chelation therapy to remove potentially harmful metal ions from the body of an individual is today frequently proposed as a means for gaining and maintaining good health and avoiding surgery for heart disease. Although chelation therapy of human patients is most commonly carried out by intravenous injection, oral chelation therapy is also well known. For example, U.S. Pat. No. 5,080,906 to Carenzi et al. discloses a method and composition for oral administration of N-acetylcysteine (NAC).

Various formulations containing one or more chelators for oral administration are commercially available. Typically, these formulations contain a low dosage of chelators, along with a mixture of other purportedly beneficial ingredients. The list of ingredients for one such product, Life Glow Plus™ from Vibrant Life contains, per capsule, 25 mg disodium dihydrate EDTA, 15 mg L-cysteine, and 15 mg NAC, and specified amounts of 48 additional substances, including other amino acids, vitamins, minerals, herbs, glandular substances, and "special items." The recommended daily dosage of Life Glow Plus™ is 20 capsules.

Another available oral chelation product is Kelation Plus® from Kelation Plus International, Jacksonville Fla., a powder packaged in individual daily servings and said to contain 26 pharmaceutical grade vitamins, minerals, amino acids, and glandulars. The list of 26 ingredients, all in unspecified amounts, for Kelation Plus® includes L-cysteine. A footnote to the ingredients list states: "EDTA used as a preservative."

There remains a need for a convenient, orally administered pharmaceutical composition that contains an effective dosage of chelators without included extraneous ingredients that may impair their effectiveness. This need is met by the present invention.

SUMMARY OF THE INVENTION

In accordance with the present invention, a solid pharmaceutical composition for the oral administration of chelating agents to an individual consists essentially of: at least 100 milligrams of ethylenediaminetetraacetic acid (EDTA) or a molar equivalent amount of pharmaceutically acceptable salts or hydrated salts of EDTA, at least 75 milligrams of N-acetyl-L-cysteine, and an appropriate amount of at least one pharmaceutical formulating agent.

The pharmaceutical composition of the present invention provides a convenient alternative to intravenous injection of chelating agents, which is time-consuming and requires visitation to a medical facility.

DETAILED DESCRIPTION OF THE INVENTION

The solid pharmaceutical composition of the present invention can be in the form either of a tablet or, preferably, a capsule and contains at least 100 milligrams of ethylenediaminetetraacetic acid (EDTA), or a molar equivalent amount of pharmaceutically acceptable salts or hydrated salts of EDTA, and at least 75 milligrams of N-acetyl-L-cysteine (NAC). EDTA has a formula weight is 292. Inclusion of a salt or hydrated salt rather than EDTA itself in the composition requires that the amount of the EDTA component be adjusted upwards. For example, about 127 milligrams of the disodium salt dihydrate of EDTA, whose formula weight is 372, is the molar equivalent of 100 milligrams of EDTA.

Preferably, the pharmaceutical composition of the present invention contains at least 200 milligrams of ethylenediaminetetraacetic acid (EDTA) or a molar equivalent amount of its salts or hydrated salts, and at least 150 milligrams of N-acetyl-L-cysteine (NAC). More preferably, the composition contains at least 380 milligrams of ethylenediaminetetraacetic acid (EDTA) or a molar equivalent amount of its salts or hydrated salts, and at least 300 milligrams of N-acetyl-L-cysteine (NAC). Especially preferred is a composition containing at least 500 milligrams of ethylenediaminetetraacetic acid disodium salt dihydrate ($Na_2EDTA.2H_2O$) and 300 milligrams of N-acetyl-L-cysteine (NAC). The usual daily dose for an individual is one or two capsules containing this especially preferred composition.

In addition to the recited amounts of the two chelators, the solid pharmaceutical composition of the present invention contains an appropriate amount of at least one pharmaceutical formulating agent, which is required to put the composition in tablet or capsule form. Such materials, which may be present in the composition in a total amount of up to about 5 weight percent, include, for example, fillers, flow agents, colorants, flavorings, and the like, all well known in the art. In the composition of the present invention, which preferably is in the form of a gelatin capsule, a flow agent is particularly useful. Preferred flow agents include magnesium stearate, silica, and mixtures thereof.

The invention has been described in detail for the purpose of illustration, but it is understood that such detail is solely for that purpose, and variations can be made by those skilled in the art without departing from the spirit and scope of the invention, which is defined by the following claims.

What is claimed is:

1. A solid pharmaceutical composition for the oral administration of chelating agents to an individual, said composition consisting essentially of: at least 100 milligrams of ethylenediaminetetraacetic acid (EDTA) or a molar equivalent amount of pharmaceutically acceptable salts or hydrated salts of EDTA, at least 75 milligrams of N-acetyl-L-cysteine (NAC), and an appropriate amount of at least one pharmaceutical formulating agent.

2. The composition of claim 1 containing at least 200 milligrams of ethylenediaminetetraacetic acid (EDTA) or a molar equivalent amount of pharmaceutically acceptable salts or hydrated salts of EDTA and at least 150 milligrams of N-acetyl-L-cysteine (NAC).

3. The composition of claim 2 containing at least 380 milligrams of ethylenediaminetetraacetic acid (EDTA) or a molar equivalent amount of pharmaceutically acceptable salts or hydrated salts of EDTA and at least 300 milligrams of N-acetyl-L-cysteine (NAC).

4. The composition of claim 3 containing at least 500 milligrams of ethylenediaminetetraacetic acid disodium salt dihydrate ($Na_2EDTA.2H_2O$) and 300 milligrams of N-acetyl-L-cysteine (NAC).

5. The composition of claim 1 contained in a tablet or a capsule.

6. The composition of claim 5 contained in a gelatin capsule.

7. The composition of claim 1 wherein said pharmaceutical formulating agent is present in said composition in a total amount up to about 5 weight percent.

8. The composition of claim 1 wherein said pharmaceutical formulating agent is a flow agent.

9. The composition of claim 8 wherein said flow agent is selected from the group consisting of magnesium stearate, silica, and mixtures thereof.

* * * * *